Figure 1:
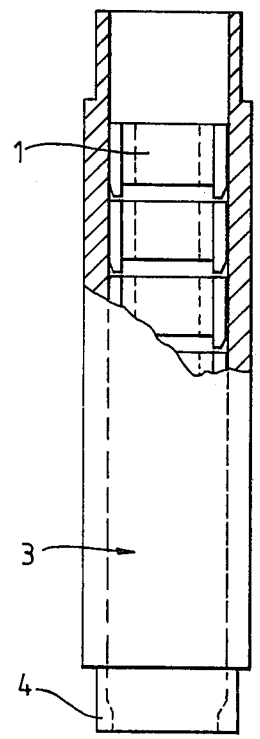
Figure 1:
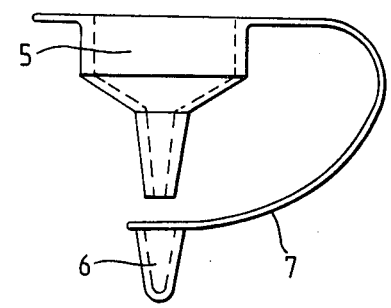

United States Patent [19]

Suovaniemi et al.

[11] 4,398,382
[45] Aug. 16, 1983

[54] METHOD FOR WASHING AND COATING AS WELL AS FOR DOSAGE OF EIA-RINGS AND A DEVICE FOR CARRYING OUT THE METHOD

[75] Inventors: Osmo A. Suovaniemi; Jukka Tervamäki; Jukka Suni; Paul Partanen, all of Helsinki, Finland

[73] Assignee: Kommandiittiyhtio Finnpipette Osmo A. Suovaniemi, Finland

[21] Appl. No.: 252,180

[22] Filed: Apr. 8, 1981

[30] Foreign Application Priority Data

Apr. 28, 1980 [FI] Finland ............................. 801355

[51] Int. Cl.³ ..................... B65B 3/00; C12M 1/00; B01L 11/00
[52] U.S. Cl. ........................................ 53/431; 53/474; 134/25.4; 134/117; 206/303; 221/267; 422/99; 435/7; 435/287; 435/317; 436/807
[58] Field of Search ............... 23/230 B, 915, 920; 422/99, 102; 435/7, 287, 317; 221/267, 279; 128/217, 218 C, 235, 236, 237, 238, 264; 134/21, 25.4, 26, 117; 436/807; 206/303; 53/431, 474

[56] References Cited

U.S. PATENT DOCUMENTS

| | | | |
|---|---|---|---|
| 747,444 | 12/1903 | La Veine | 128/264 |
| 1,679,391 | 8/1928 | Aas | 128/264 |
| 2,601,852 | 7/1952 | Wendt | 128/264 |
| 3,932,141 | 1/1976 | Beall et al. | 422/102 |
| 4,053,284 | 10/1977 | Posch | 23/230 B X |
| 4,062,652 | 12/1977 | Rolfo-Fontana | 435/7 X |
| 4,086,914 | 5/1978 | Moore | 128/264 X |
| 4,113,143 | 9/1978 | Spagnola, Jr. | 221/267 |
| 4,146,365 | 3/1979 | Kay et al. | 23/230 B X |

Primary Examiner—Arnold Turk
Attorney, Agent, or Firm—Hopgood, Calimafde, Kalil, Blaustein & Judlowe

[57] ABSTRACT

A method and apparatus for washing the solid annular pieces used in immune methods, i.e. the so-called EIA-rings, and for coating such rings with a reagent, as well as for the dispensing of the rings. The EIA-rings are fitted, one after the other, into a tubular container part, which is open at both ends. To the bottom end of the container part an intake tip is attached, and to the other end a device for drawing and exhausting a liquid through the intake tip into the container part. The container part enclosing the EIA-rings is then sealed at both ends until the upper end of the container part is opened for dispensing the rings. The opened end is connected to a dosage device, the intake tip of the container part is removed and the EIA-rings are dispensed by means of the device.

3 Claims, 4 Drawing Figures

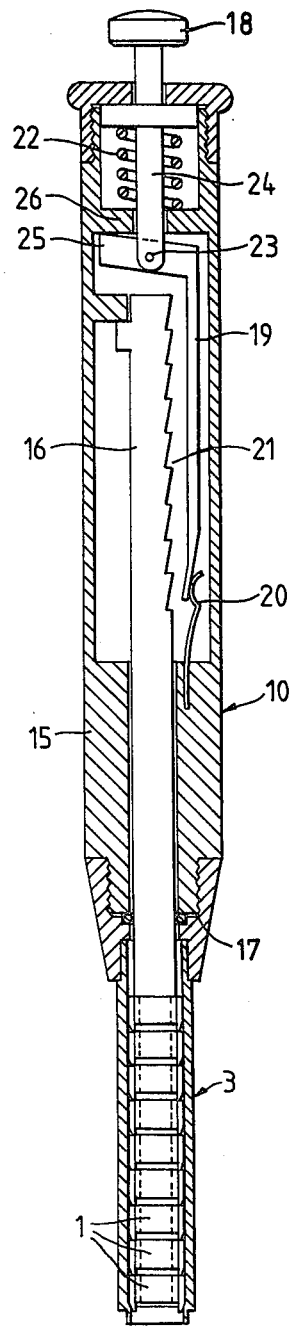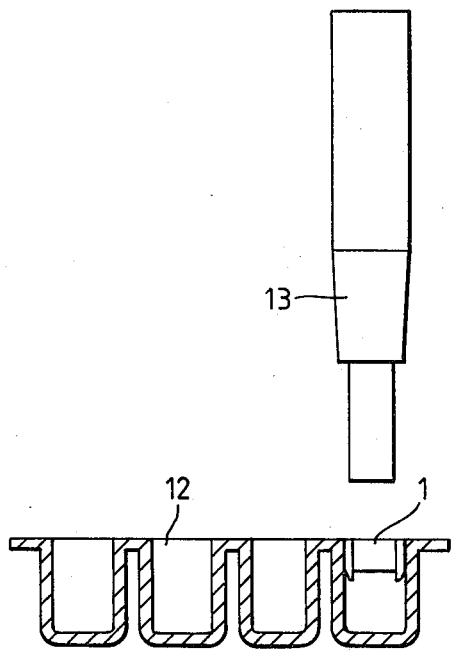
Fig.3.
Fig.4.

METHOD FOR WASHING AND COATING AS WELL AS FOR DOSAGE OF EIA-RINGS AND A DEVICE FOR CARRYING OUT THE METHOD

The subject of the present invention is a method for washing the solid annular pieces to be used in immune methods, i.e. the so-called EIA-rings, for coating such rings with a reagent, such as, e.g., an antigen or antibody solution, as well as for the dosage of the said EIA-rings.

The EIA-ring is intended to be used as the solid phase in immune methods. Its objective is to provide readiness for the selection of optimum solid-phase raw - materials. The EIA-rings must be sensitized, i.e. coated with a reagent, before they are taken into use, and the object of the present invention is to provide a method and an equipment by whose means the application of the reagents to the EIA-rings can be performed conveniently and safely. In order that the result of coating of the EIA-rings should be good, after sensitizing the rings cannot be handled by means of external applicators without risking the reliability of the result of the method. The EIA-rings must be dosed into the reaction vessel or straight into the combined reaction and measurement vessel as easily as possibly without damaging the reagent applied to the ring.

The present invention permits purposeful washing and coating as well as successful dosage of EIA-rings, and the method in accordance with the invention is mainly characterized in that the EIA-rings are fitted, one after the other, into a tubular container part, which is open at both ends and to whose bottom end an intake tip is attached and to the other end an equipment by means of which a liquid, such as a detergent solution or coating solution, is sucked through the intake tip into the container part and, correspondingly, removed from the container part, and that the container part enclosing the coated EIA-rings is sealed at both ends until the upper end of the container part is opened for the purpose of dosage of the EIA-rings to the object of use and the opened end is connected to the dosage device, whereupon the intake tip of the container part is also removed and the EIA-rings are pushed out by means of the dosage device, preferably by stepwise movements corresponding the dosage of one ring at a time, from the bottom end of the container part provided with a narrowed-off portion. Another subject of the present invention is a device for carrying out the above method, and the circumstances characteristic of the device come out from claim 2.

In addition to the container tube, the equipment to be used in the method in accordance with the invention consists of two parts, by means of one of which it is possible to perform the washing and coating of the rings and, on the other hand, by means of the other one it is possible to perform the dosage of the rings into the cuvette sets. The equipment may have one or several channels, depending on the size and the dosage requirements of the rings.

The method in which the ring washing, coating and dosage apparatus or equipment is needed is known as the enzyme-immune method, but the equipment concerned can also be used in radio-, fluoro-, luminescence-, and viro-immune methods. By means of the equipment, successful performance of the method is guaranteed, because by its means it is possible to transfer the rings easily, safely and untouched by the hand. Thus, according to the present invention, a suitable applicator for the dosage of EIA-rings as well as coating and washing equipment for the performance of controlled sensitizing or coating of the EIA-rings have been developed. Even the use of a covalent bond between the reagent and the solid phase becomes possible.

Figure 2:
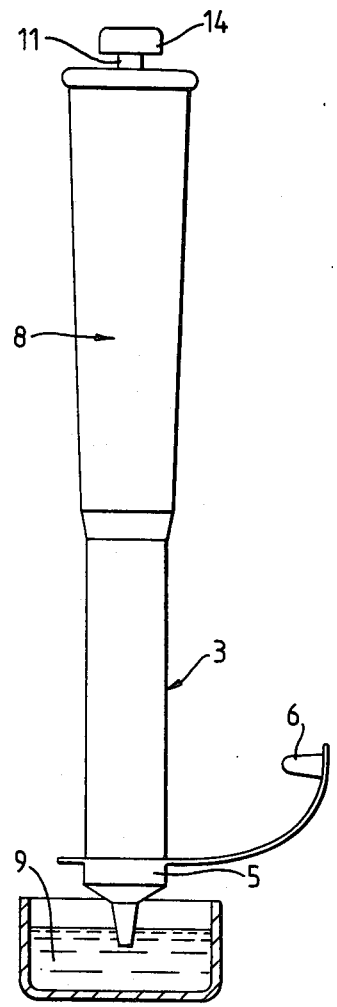

The invention comes out more closely from the following description and from the attached drawings, wherein FIG. 1 shows the container part as a side view and partly in section, FIG. 2 is a side view of the container part as connected to the device by means of which liquid is sucked into the container part, FIG. 3 is a sectional side view of the container part as connected to the dosage device, and FIG. 4 shows an EIA-ring as fitted into a cuvette set as well as a pushing means for bringing the ring into the correct position in the cuvette set.

FIG. 1 discloses a cylindrical or tubular container part 3, which is open at both ends and whose lower end is on the inside provided with such a narrowed-off portion 4 as prevents falling off of the EIA-rings 1 from the container part 3. The narrowed-off portion 4 may be an annular projection, flange or equivalent projecting from the wall of the container part towards the centre of the container part. An orificed intake tip 5, provided with a closing means 6, has been designed so as to be connected detachably onto the outer face of the bottom end of the container part 3. The closing means 6 consists of a seal cap, which is by means of a connecting band 7 fastened to the intake tip 5. The upper end of the container part 3 is provided with a closing plug 2, by means of which the container part 3 can be sealed, for example, for the time of storage or shaking.

The washing and coating equipment 8 is an equipment by means of which it is possible to suck a liquid into the container part 3 and to remove the liquid from same. The equipment 8 may consist, e.g., of a device similar to a pipette, whose bottom end is provided with a connection for the upper end of the container part 3, via which connection there is connection into the cylinder space of the equipment 8, which cylinder space is provided with a piston having a piston rod 11. After the EIA-rings 1 have been fitted one after the other into the container part 3, as is shown in FIG. 1, and the bottom end of the container part 3 has been provided with the intake tip 5, with the seal cap 6 opened as shown in FIG. 2, and after the closing plug 2 has been removed from the upper end of the container part 3, the container part 3 can be pushed by means of a friction joint into the bottom part of the washing and coating equipment 8 in the way shown in FIG. 2. Then the piston of the equipment 8 is in the lower position. As is shown in FIG. 2, liquid can be sucked from the container 9 through the intake tip 5 into the container part 3 by means of the equipment 8 by pulling the piston of the equipment 8 by means of the piston rod 11 and the knob 14 upwards. Correspondingly, the emptying of the container part 3 out of liquid takes place by pressing the piston into the lower position by the intermediate of the knob 14 and the piston rod 11. In this way it is possible to perform the coating of the EIA-rings, e.g., with an antigen or antibody solution. Likewise it is possible to perform efficient washing of the EIA-rings. The EIA-rings can be very well stored in the container part 3 when the latter is tightly closed at both ends. Then the container part may contain, e.g., coating solution or any other solution necessary from the point of view of the method. The container part 3 fits tightly into the washing and coating equipment 8, so that the intake of the solution is hygienic and safe even if the solution to be sucked in were infectious or otherwise harmful to the operator.

The device 10 of dosage of EIA-rings 1 comes out from FIG. 3, wherein the container part 3 is connected to the bottom part of the dosage device 10 by means of friction joint. Inside the frame part 15 of the dosage device 10, a push rod 16 is fitted around which there is a packing 17 in the lower part of the frame part 15, the only purpose of the packing 17 being to produce sufficient friction between the push rod 16 and the frame part 15 so that the push rod 16 is shifted in relation to the frame part 15 only by the effect of the press knob 18. In FIG. 3 the push rod 16 is in its upper position. When the press knob 18 is depressed, the push lever 19 can pivot as pressed by the spring 20 against the toothing 21 on the push rod 16, and when the press knob 18 is depressed further, the push lever 19 pushes the push rod 16 downwards by means of the toothing 21, and the push rod 16 pushes the EIA-rings 1 in the container part 3 in front of the push rod. One depression of the press knob 18 may correspond, e.g., the shifting of one tooth distance by means of the push rod 16, whereby the tooth distance shall equal the height of an EIA-ring 1. After the depression of the press knob 18, the spring 22 restores the press knob back to the upper position. Since the push lever 19 is attached to the press knob rod 24 by means of an articulated joint 23, the push lever 19 also rises to the upper position. When the upper end 25 of the push lever 19 meets the flange 26 on the frame part 15 of the dosage device 10, the push lever 19 is pivoted apart from the toothing 21 of the push rod 16. By repeatedly depressing the press knob 18 it is possible to dose EIA-rings 1 from the container part 3, e.g., into a cuvette or tube or cuvette set or tube set, etc. After the dosage has taken place, the container part 3 is detached from the dosage device 10 and the push rod 16 of the dosage device is pushed to the upper position ready for new dosage. The dosage device may also be constructed so that it pushes several EIA-rings out at a time, if such an arrangement is required. The objective of the dosage device 10 is to permit dosage of the rings 1 untouched by the hand - like the coating and washing of the rings above. The equipment may, of course, also be made automatic by using applications of electronics for controlling the mechanical components, e.g. by means of a microprocessor.

The container part 3 is, of course, selected in accordance with the size of the EIA-rings to be dosed.

The equipment further comprises a pusher 13 in accordance with FIG. 4, by means of which the EIA-ring 1 dosed by the dosage device 10 can be pushed onto the bottom of the tube, cuvette 12 or any other vessel used in the method safely and without damaging the coating of the ring.

What is claimed is:

1. A method of contacting with a liquid solution annular pieces used in research and for storing and dispensing same, comprising the steps of:
    (I) the liquid contacting steps including:
        (a) fitting said annular pieces in a tubular container means, said container means stacking said annular pieces, said container means having upper and lower ends and being open at both ends and including retention means at the lower end for preventing said annular pieces from falling from said container;
        (b) fitting said upper end of said container to a liquid intake and discharge means;
        (c) fitting said lower end of said container means with releasable tip means;
        (d) drawing said liquid solution into said container means by said liquid intake and discharge means;
        (e) exhausting said liquid solution from said container by said liquid intake and discharge means;
    (II) the storing steps including:
        (f) removing said liquid intake and discharge means from said container means;
        (g) releasably capping the upper end of said container means and the lower end of said tip means;
    (III) the dispensing steps including:
        (h) removing the caps and tip means;
        (i) fitting said container means to a dispensing means, said dispensing means including means for selectively overcoming said retention means; and
        (j) dispensing said rings from said container.
2. A device for storing, contacting with a liquid and dispensing annular pieces, said device comprising:
    (a) tubular container means for holding a stack of annular pieces, said tubular means having upper and lower portions, said lower portion of said tubular means including retention means to prevent said stack from falling from said container;
    (b) intake tip means releasably engagable with the lower portion of said container means, said tip means including an orifice for liquid passage;
    (c) syringe means for drawing and exhausting liquid into and out of said container means to contact said pieces with said liquid, said syringe means being releasably engagable with said container means;
    (d) dispensing means for displacing said rings downwardly out of said container means and overcoming said retention means to dispense said rings, said dispensing means being releasably engagable with said container means; and
    (e) cap means releasably engagable with the upper end of said container means and the lower end of said tip means to permit said container to be stored.
3. The device as claimed in claim 2, wherein said dispensing means includes a handle portion, rod means slidably displaceable within said handle portion and extending out of said handle portion, the external portion of said rod means insertable within said container means and engagable with said stack of annular pieces, and manually operable means for sliding said rod means to displace and dispense said annular pieces.

* * * * *